United States Patent
Cardelius

(10) Patent No.: US 8,381,574 B2
(45) Date of Patent: Feb. 26, 2013

(54) REDUCTION OF PRESSURE INDUCED TEMPERATURE INFLUENCE ON THE SPEED OF SOUND IN A GAS

(75) Inventor: Erik Cardelius, Djursholm (SE)

(73) Assignee: Maquet Critical Care AB, Solna (SE)

( * ) Notice: Subject to any disclaimer, the term of this patent is extended or adjusted under 35 U.S.C. 154(b) by 397 days.

(21) Appl. No.: 12/842,364

(22) Filed: Jul. 23, 2010

(65) Prior Publication Data

US 2010/0281949 A1 Nov. 11, 2010

Related U.S. Application Data

(62) Division of application No. 11/917,414, filed on Dec. 13, 2007, now Pat. No. 7,784,327.

(51) Int. Cl.
 *G01N 29/02* (2006.01)
(52) U.S. Cl. ........... 73/24.01; 73/1.06; 73/1.02; 73/23.2
(58) Field of Classification Search ............... 73/24.01, 73/23.2, 25.01, 1.06, 1.02, 23.25, 1.01
See application file for complete search history.

(56) References Cited

U.S. PATENT DOCUMENTS

| | | | |
|---|---|---|---|
| 4,155,246 | A | 5/1979 | Dempster et al. |
| 4,791,922 | A | 12/1988 | Lindsay-Scott et al. |
| 4,932,255 | A | 6/1990 | Brace et al. |
| 4,938,066 | A | 7/1990 | Dorr |
| 5,060,506 | A | 10/1991 | Douglass |
| 5,351,522 | A | 10/1994 | Lura |
| 5,687,709 | A | 11/1997 | Akerberg |
| 5,694,924 | A | 12/1997 | Cewers |
| 6,114,700 | A * | 9/2000 | Blades .......................... 250/343 |
| 6,131,571 | A | 10/2000 | Lampotang et al. |
| 6,202,468 | B1 | 3/2001 | Dempster et al. |
| 6,213,120 | B1 | 4/2001 | Block et al. |
| 6,481,288 | B1 | 11/2002 | Humphrey et al. |
| 2004/0093948 | A1 | 5/2004 | Kelner et al. |
| 2010/0174124 | A1* | 7/2010 | Tonkovich et al. ............. 585/23 |

FOREIGN PATENT DOCUMENTS

| | | |
|---|---|---|
| EP | 1 083 427 A2 | 3/2001 |
| EP | 1 336 841 A2 | 8/2003 |
| EP | 1 343 004 A2 | 9/2003 |
| EP | 1 464 957 A2 | 10/2004 |
| GB | 2 195 767 | 4/1988 |
| JP | 3205555 | 9/1991 |
| WO | WO 01/08554 A1 | 2/2001 |

OTHER PUBLICATIONS

Patent Abstracts of Japan Publication No. 2002257801 A, for Japanese Application 2001111990.
"A Sonar-Based Technique for the Ratiometric Determination of Binary Gas Mixtures," Nuclear Instruments and Methods in Physics Research, vol. A364 (1988), pp. 219-234.

* cited by examiner

*Primary Examiner* — Hezron E Williams
*Assistant Examiner* — Rodney T Frank
(74) *Attorney, Agent, or Firm* — Schiff Hardin LLP

(57) ABSTRACT

An apparatus for determining the proportion of gases in a gas mixture, has a measurement chamber having a chamber defining structure, a gas inlet and a gas outlet, an ultrasound source and an ultrasound detector mounted such that the ultrasound source is capable of transmitting ultrasound through the chamber to the ultrasound detector; a temperature sensor mounted such that the sensor is capable of sensing the temperature in the chamber. The chamber defining structure is adapted to amplify thermal exchange with a gas content in the chamber so as to suppress a temperature change in the chamber.

15 Claims, 10 Drawing Sheets

REDUCTION OF PRESSURE INDUCED TEMPERATURE INFLUENCE ON THE SPEED OF SOUND IN A GAS

RELATED APPLICATION

The present application is a divisional application of Ser. No. 11/917,414, filed on Dec. 13, 2007 now U.S. Pat. No 7,784,327.

BACKGROUND OF THE INVENTION

1. Field of the Invention

The present invention relates in general to the measurement of speed of sound in a gas mixture. More particularly, the present invention relates to applications of ultrasound detectors for example in the measurement of gas concentration or gas flow in environments where pressure induced temperature influence is a dominant factor for measurement accuracy.

2. Description of the Prior Art

In some applications of ultrasound detection, such as the measurement of concentration or proportions of gas components in a gas mixture, pressure variations in the gas mixture has a large influence on the measurement accuracy. There is a well known connection between the speed of sound and gas specific parameters, and, based on this connection and measurement values of the speed of sound, a current proportion of gas content can be calculated. Furthermore, the speed of sound in a gas has a strong dependency on temperature, and in order to correctly calculate the gas content a timely and accurate temperature measurement on the gas is also required.

In medical breathing apparatuses it is of vital importance that gas proportions in for example inspiration or expiration air from a patient is accurately determined for the purpose of monitoring and controlling the dosing of gas components in a gas mixture or for monitoring the health state of a patient. However, when a patient is breathing, significant changes in pressure occur in the breathing apparatus and consequently, in accordance with the ideal gas law, the temperature of the gas varies largely. Thus, in order to accurately determine the proportions of the gas content it is generally required that a very precise temperature measurement is carried out, and that the temperature measurement and the sound speed measurement are carried out closely in time such that they describe the momentary physical state of the gas.

When measuring temperature in actual practice there is always a certain degree of delay in the temperature measurement in relation to the real current temperature. The delay depends on the time constant of the temperature sensor that is used for the measurement. The delay in the ultrasound sensor depends on the sampling frequency and is in general so short that it is insignificant and negligible in comparison with the temperature measurement. A concurrent measurement of sound speed and temperature will therefore always result in a, to some degree, erroneous temperature that in its turn causes an erroneously calculated gas concentration.

A number of different approaches are known to deal with this measurement problem. Examples are described in the following publications, which are all incorporated by reference in the present application.

In the technical report *A SONAR BASED TECHNIQUE FOR THE RATIOMETRIC DETERMINATION OF BINARY GAS MIXTURES*, G. Hallewell et al, Nuclear Instruments and Methods in Physics Research A264 (1988) 219-234, North-Holland, Amsterdam, there is a theoretical background to this kind of measurement.

U.S. Pat. No. 6,202,468 discloses an apparatus and a method for determining the relative proportions of gases in a mixture by measuring magnetic susceptibility and speed of sound.

U.S. Pat. No. 4,155,246 discloses a gas analyzing system using sonic wave shift over a tubular gas column. U.S. Pat. No. 4,932,255 discloses a method and device for measuring on a gas flow using surface acoustic waves over a substrate positioned in the gas flow. Thermally conductive paths around the substrate periphery reduce thermal gradients. In this piece of prior art the thermally conductive paths are devised in order to reduce thermal gradients that are created by the sensor in connection with transmission of surface acoustic waves.

U.S. Pat. No. 5,351,522 discloses an ultrasound detection based gas sensor with an L-shaped measurement chamber. This piece of prior art is directed to the problem of minimizing standing sound waves in the measurement chamber.

JP 2002 257 801 discloses an ultrasonic gas analysis sensor which deals with the problems of avoiding effects on the sound waves due to gas flow rate and diffusion. A measurement chamber with diffusion holes is positioned in a gas passage tube with a gas inlet and outlet.

EP 1 083 427 discloses a method for determining the gas content of for example oxygen in breathing gas be means of measuring speed of sound. Problems caused by temperature variations are dealt with by synchronising sound speed detection with one or a plurality of specific times in a respiratory cycle.

EP 1 336 841 discloses a method for determining the temperature in an acoustic gas meter by means of an elongate resistive temperature sensor positioned in the ultrasound propagation region of the gas meter.

GB 2 195 767 discloses concentration measurement of a substance, such as a liquid, using ultrasonic pulses and detection of an nth echo.

U.S. Pat. No. 5,060,506 discloses a method and an apparatus for measuring the ratio of gases in a two gas mixture such as a therapeutic oxygen/nitrogen mixture. The gas mixture is passed through a sample tube within which ultrasound waves travel in successive bursts of pulses at the resonant frequency of the transmitter/receiver pair. Between bursts is a quiescent time period having a duration that is long enough to assure dissipation of transients so that standing waves do not form. The delay caused by the transit time of the sound through the gas sample generates electrical pulses that are translated into an analogue signal which is then temperature-corrected. The resulting voltage is proportional to the transit time and thus to the gas composition. The sample tube is contained inside a larger cylindrical body to enhance the gas flow and provide thermal insulation which is intended to improve the accuracy of temperature compensation.

U.S. Pat. No. 4,938,066 discloses a method and apparatus dealing with the problem of length expansion in an acoustic sensor with an ultrasound transducer emitting sound pulses that are reflected against a proximate surface of an invar rod and against a second surface at the distal end of the invar rod. The time difference between detection of reflected pulses from the respective surfaces and the known length of the rod are used to calculate the speed of sound.

U.S. Pat. No. 6,481,288 discloses a method and apparatus for measuring the speed of sound employing a spherical measurement chamber.

SUMMARY OF THE INVENTION

An object of the present invention is to further improve the accuracy in sound speed detection based measurement devices and methods in a gas mixture in environments where pressure induced temperature influence is a dominant factor for measurement accuracy.

There are, inter alia, the following aspects of the object and the problem:

- To decrease the influence of pressure variations on the temperature of a portion of a gas mixture currently subjected to measurement.
- To provide an appropriate sound pattern from an ultrasound transmitter in the measurement device.
- To decrease influence from thermal expansion of material in the measurement device.
- To determine gas concentration in a gas mixture.
- To determine flow rate in a gas flow.

In accordance with the invention the above object is achieved by equilibrating temperature change in a portion of the gas or gas mixture that is currently being subjected to measurement, and thereby suppress temperature variations in the gas. In other words, the invention solves the problem by counteracting and levelling out temperature gradients in a sensor arrangement caused by the measured entity, i.e. the measurement object in the shape of a gas mixture.

As mentioned in the background, the temperature of the gas changes rapidly during pressure changes, which for example in a typical application of the present invention in medical breathing apparatuses occur in the tubing system in connection with inspiration or expiration ventilation of a patient. Concurrently with the temperature change in the gas there is a process of levelling out or equilibrating the temperature change of the gas towards an average temperature by thermal exchange between surrounding matter and the gas.

The invention is based on the insight that the speed of the levelling out process can be increased to such a degree that the influence of temperature gradients due to pressure changes in the gas are minimized and even negligible. In accordance with the invention, acoustic gas measurement is therefore devised such that thermal exchange is amplified and the speed of the levelling out process is matched with predetermined requirements on the time lag of equalization of a temperature change in the gas. This is in contrast with prior art, in which e.g. measurement speed is increased or sudden temperature changes are compensated for in calculations in order to handle measurement problems due to pressure induced temperature changes. In the invention, the measurement chamber itself is adapted so as to decrease or even eliminate these measurement problems.

In accordance with the invention, the thermal exchange is amplified by making the gas measured upon come into close contact with solid surfaces of a thermally inert and thermally well conducting matter so that heat can move freely from the gas to surrounding structure. In an implementation of the inventive concept, the invention is achieved by providing a measurement chamber that is devised with a structure adapted to amplify the thermal exchange between a portion of the gas that is currently present in the chamber and the chamber defining structure. The technical effect of this is that when fast energy pulses that occur in the shape of pressure variations are introduced into the system of tubing and connected equipment, the measurement chamber will operate as a low pass filter for the energy pulses and the matter in the chamber will present small variations around an average temperature. Due to the amplified thermal exchange between the chamber matter and the gas, the gas will also be low pass filtered in this respect and temperature variations will be levelled out so fast that they become negligible in this context.

Preferably, the chamber defining structure is adapted to provide thermal exchange such that a temperature change is equalized to a predetermined level within a predetermined time lag. The time lag is for example defined as the time constant for thermal exchange of the chamber defining structure. The chamber defining structure is for example adapted to provide the required thermal exchange efficiency dependent on a predetermined maximum error in gas concentration rate. This is embodied as a method of dimensioning a measurement device within the inventive concept.

The speed of the temperature change levelling out process in fact depends on a number of parameters such as the thermal conductivity of the gas, the geometric distance from gas molecules to the surfaces of surrounding matter, the thermal inertia and the thermal conductivity of the surrounding matter. The geometrical distance and the thermal conductivity have been found to be the dominant parameters with regard to the present invention.

In accordance with a first aspect of the invention, temperature equilibrium is achieved by designing the measurement chamber with a relation between the shape of a cavity in the chamber and the properties of material defining the cavity. According to this aspect, a chamber defining structure is adapted with a combination of shape, size and material in relation to properties of the gas mixture to be used in a particular application of the invention. Preferably, this adaptation is devised such that the time lag for thermal exchange between the gas mixture and the measurement apparatus is less than or equal to ($\leqq$) a predetermined maximum allowable time lag for thermal exchange. A maximum allowable time lag for thermal exchange is preferably calculated dependent on a maximum allowable error in the determined proportion of a gas in the gas mixture and the magnitude of occurring temperature variations in the gas mixture. In an embodiment, the maximum allowable time lag is calculated also dependent on the time lag of a signal filter for application on a signal from an ultrasound detector in the measurement device.

According to a second aspect, the influence from expansion of the material in the measurement device is decreased by mounting the ultrasound transducer in the measurement chamber such that influence from expansion in the transducer is eliminated.

According to a third aspect, structure borne sound originating from the ultrasound transducers is reduced by means of an acoustically dampening sealing member placed between the end surface of the measurement chamber openings and the active surface of the transducers. The sealing member is preferably made in silicon rubber.

According to a fourth aspect of the invention, the resolution of measurement in a small size measurement chamber with a short distance between ultrasound transducers is improved by allowing an ultrasound to bounce between transducer surfaces and detecting the nth echo. Thereby the ultrasound pulse travels a longer distance.

According to a fifth aspect of the invention, the pattern of ultrasound transmitted through the gas in the measurement chamber is devised in order to decrease transients and render a harmonious transient steady-state process. This is achieved by repeatedly transmitting bursts of pulse trains and starting each train with a ¼ pulse period. This entails that the frequency applied to the transducer is not equal to the resonance frequency of the transducer in a mathematical sense.

Further aspects of the invention are explained in the detailed description of embodiments.

In addition to the above mentioned technical effects and advantages, the invention also entails the following.

A simple temperature sensor with a comparatively large time constant can be used in the measurement device since the speed of temperature changes is decreased through the temperature equilibrating effect.

The inventive measurement device is an environmentally more friendly technical alternative to carbon-combustion cell (fuel cell, electrochemical cell) based sensors. Such sensors have to be replaced once a year, and produce a significant amount of lead waste.

Furthermore, the invention enables an alternative to paramagnetic sensors that are not only expensive but also mechanically sensitive.

In this text the term equilibrating as well as synonymous expressions such as equalizing, level out and the like are used to describe the activity of exchanging thermal energy in order to suppress temperature gradients in the measured portion of the gas.

Gas and gas mixture are expressions used to describe the gas entity that is measured upon. A typical gas mixture in medical breathing apparatus applications is a so called binary gas composed of a normal air mixture and some other gas such as oxygen or nitrogen.

The invention concerns determining and monitoring the concentration of a gas component in a gas mixture. There are various alternative expressions for this, e.g. proportion of gases, relative proportions of gases, gas content and the like.

In methods for determining the proportions of gases in a binary gas mixture, i.e. a mixture of two gases, the following well known relation can be used. The speed of sound in a gas mixture can be described according to the equation:

$$c = \sqrt{\frac{c_p^* R_M T}{c_v^* M^*}} \quad [\text{eq. 1}]$$

where c=speed of sound [m/s]
cp=specific heat at constant pressure [kJ/kgK]
cv=specific heat at constant volume [kJ/kgK]
Rm=gas constant 8314.5 [J/kmolK]
T=temperature [K]
M=molecular weight, and where $c_p$, $c_v$ och M (molecular weight) of a gas has been replaced with the corresponding values for a mixture of gases taken from tables of physical properties gases. The replacing quantities $c_p^*$, $c_v^*$ och $M^*$ depend on the proportion of gases. The current concentration of one of the gases can be calculated by resolving the equation for $M^*$ in a per se known manner.

The time constant is generally the time required for an instrument to indicate a given percentage of the final reading resulting from an input signal; the relaxation time of an instrument. In the case of instruments such as thermometers, whose response to step changes in an applied signal is exponential in character, the time constant is equal to the time required for the instrument to indicate 63.2 percent of the total change, that is, when the transient error is reduced to 1/e of the original signal change. Also called lag coefficient. [Source: Webster's on-line dictionary] In the invention a time lag can for example be defined as the time constant. In the description of embodiments of the present invention a time constant tau is defined for the measurement chamber according to this definition.

DESCRIPTION OF THE PREFERRED EMBODIMENTS

In preferred embodiments, the invention is realized by means of a measurement chamber for momentarily housing the gas that is to be measured upon. Preferably, the chamber is mounted such that a gas flow passes through the chamber and measurement samples are made intermittently on the flowing gas. A functional requirement on the measurement chamber is that the chamber defining matter shall operate as a thermal buffer and have an efficient thermal exchange with the gas molecules. The better efficiency in thermal exchange is achieved, the more the speed of the temperature equilibrating process is increased, and the better effect of the invention.

Figure 1:
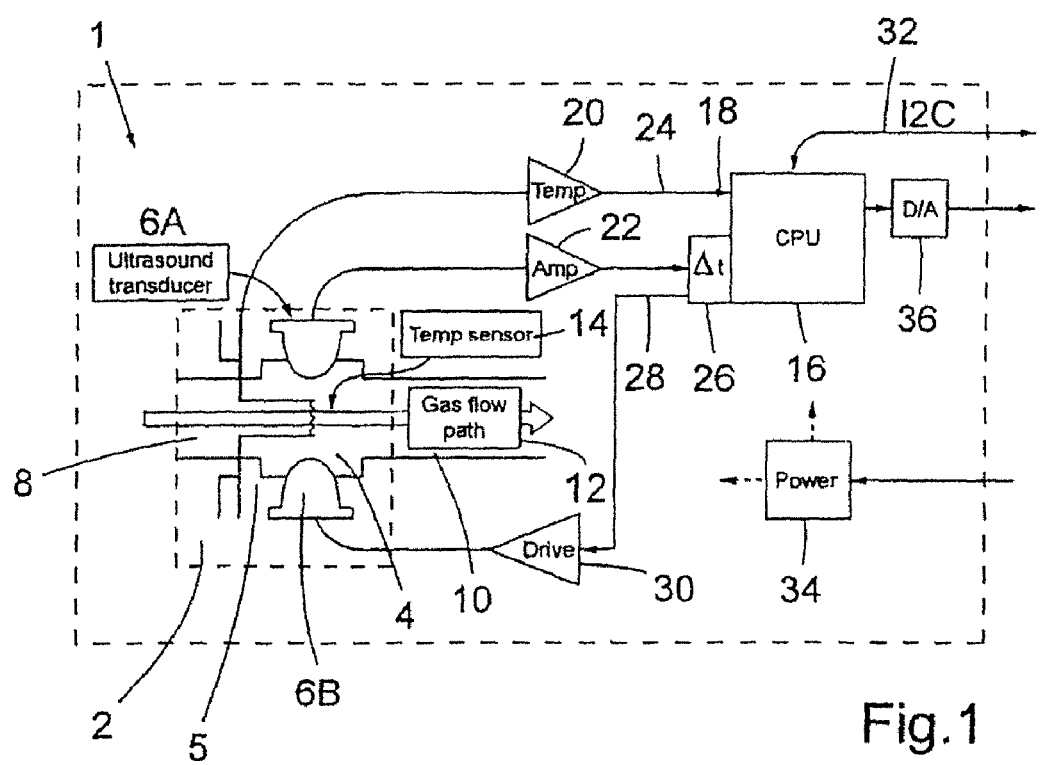
FIG. 1 shows a schematic overview of a measurement system in accordance with an embodiment of the invention.

FIG. 1 shows schematically a measurement arrangement 1 in accordance with the invention. A measurement chamber 2 defined by a chamber defining structure 5 has a cavity 4 with space for gas in which ultrasound propagate from an ultrasound transmitter to an ultrasound receiver. In the embodiment of FIG. 1 the ultrasound propagates between two oppositely mounted first and second ultrasound transducers 6A, 6B that have transmitter as well as receiver functionality in a per se known manner. The chamber is provided with a gas inlet 8 and a gas outlet 10 devised for passing gas from a gas flow path 12 through the cavity 4 of the measurement chamber 2. A temperature sensor 14 is devised for detecting the temperature of the gas in the chamber. The temperature must be measured in the proper region, i.e. the region through which the sound propagates. This can for example be achieved by means of a temperature sensor comprising a thin platinum thread that is strained through the measurement region. An alternative is to sense the temperature at a point having a known relation to the sound measurement region and calculating the temperature in the gas. Preferably, a temperature sensor that has as small time constant as possible should be selected. The exemplifying platinum temperature sensor has a short time constant and is a suitable choice for realisation of the invention. However, the invention has the effect that temperature variations are levelled out by means of efficient temperature exchange so that the temperature variation is low pass filtered and therefore a simple temperature sensor with a comparatively large time constant can be used. A currently preferred embodiment is provided with a standard NTC type termistor (NTC=Negative Temperature Coefficient).

In FIG. 1 there is also a schematic block diagram of an electronic control circuit according to one embodiment. A central processing unit CPU 16 is provided with program code specifically adapted to the invention and is via a temperature signal input 18 and a temperature signal amplifier 20 coupled to the temperature sensor 14. The first ultrasound transducer 6A is via an ultrasound receiver signal amplifier 22 coupled to an input 24 of a timer stage 26. The second ultrasound transducer 6B is via an ultrasound transmitter drive signal amplifier 30 coupled to an output 28 of the timer stage 26. The timer stage is coupled to or is realised by means of the central processing unit 16, and has the function to register and compare the time of arriving detector signals from the receiving ultrasound transducer 6A, the time difference between signals and the time of outputting drive signals for exciting the emitting ultrasound transducer 6B. A digital/analogue (D/A) converter 36 is coupled to the central processing unit for outputting for example measurement results on a display, or for producing alarm signals. The signals from the ultrasound transducers 6A, 6B are also passed through or applied in a not shown signal filter that has a certain time lag, usually expressed in terms of a time constant. The central processing unit 16 is further coupled to an I2C-bus 32 for communication with other circuit components. A power supply 34 is coupled to the components as required. The sensor arrangement is thus operated to send an ultrasound pulse through the gas mixture in the chamber, for example a mixture of air and oxygen, and the propagation time for the pulse is measured. The measured time corresponds to a timer value in the processor, for example the number 4534. Together with the measured temperature of the gas, a gas concentration rate is calculated in accordance with pre-programmed relations, and an output signal is generated in the shape of an analogue voltage for example corresponding to 21-100% oxygen O2.

The cavity 4 of the chamber 2 is defined and delimited by a physical chamber defining structure 5 designed with an appropriate shape and with an appropriate material and having surfaces that come into contact with gas streaming through the chamber.

The thermal conductivity of the structure determines the speed of thermal exchange and depends on properties of the material, shape and physical dimensions of the structure. Thermal conductivity is in the SI system of units measured in watts per meter-Kelvin, (W·m$^{-1}$·K$^{-1}$), which for materials is known from tables. For shape and physical dimensions thermal conductivity is for example estimated with indirect methods such a modelling and experimental measuring of dependent parameters. The material of the structure should thus have a high thermal conductivity and preferably be a metal such as aluminium having a thermal conductivity of 236 W·m$^{-1}$·K$^{-1}$ or steel with a thermal conductivity of about 50 W m$^{-1}$ K$^{-1}$. Other materials are also conceivable, for example heat conducting plastics added with metal chips. The weight of the thermal buffering material should be selected in relation to the other design parameters and to weight, volume and molecule density of the gas content in the chamber such that the thermal exchange efficiency is sufficient. In accordance with the invention, the available design parameters should be employed so that the chamber defining structure is adapted to provide thermal exchange such that a temperature change in the gas is equalized to a predetermined level within a predetermined time lag. It is in this context useful to define a time lag or a time constant for the thermal exchange of the chamber defining structure as a measure on the thermal exchange efficiency of the chamber.

The inventive concept concerns a method of dimensioning a measurement apparatus in accordance with the invention. The method is indirect in the sense that it approaches the dimensioning parameters from the desired accuracy of the measurement result and goes backwards to find requirements on the dimensioning parameters.

Thus, a maximum allowable error in the determined proportion of a gas in the gas mixture is determined. The allowable error depends on the application and would in an application of the invention in a breathing apparatus for example be in the range of 5% error in the a determined oxygen concentration (O2-concentration). The magnitude of maximum occurring pressure variation in the gas mixture is estimated. In the exemplifying application the maximum occurring pressure variation would for example be in the range of 50 cmH2O. In practical ventilation of a human patient, the most common pressure variations are in the range of 25-30 cmH2O. However, the pressure variations can reach extreme values up to about 100 cmH2O for example when the patient coughs.

The magnitude of maximum occurring temperature variation in the gas mixture is estimated by means of a calculation dependent on the estimated magnitude of occurring pressure variation in the gas mixture. For this estimation a model of the heat conduction process is determined and expressed as an equation comprising a term that represents the compression work performed by the varying pressure. In an exemplifying embodiment, this equation is expressed as $$\rho C_p \frac{\partial T}{\partial t} = \lambda \nabla^2 T + \dot{p} \qquad \text{Eq. 2}$$

where T is temperature, p is pressure, ρ is density, Cp is specific heat at constant pressure and λ is heat conductivity. The following mechanical and thermal parameter values are valid for air at 25° C.:

TABLE 1

| Parameter | Value |
|---|---|
| ρ | 1.18 [kg/m$^3$] |
| $C_p$ | 1000 [J/kg K] |
| λ | 0.024 [W/m K] |

Figure 12:
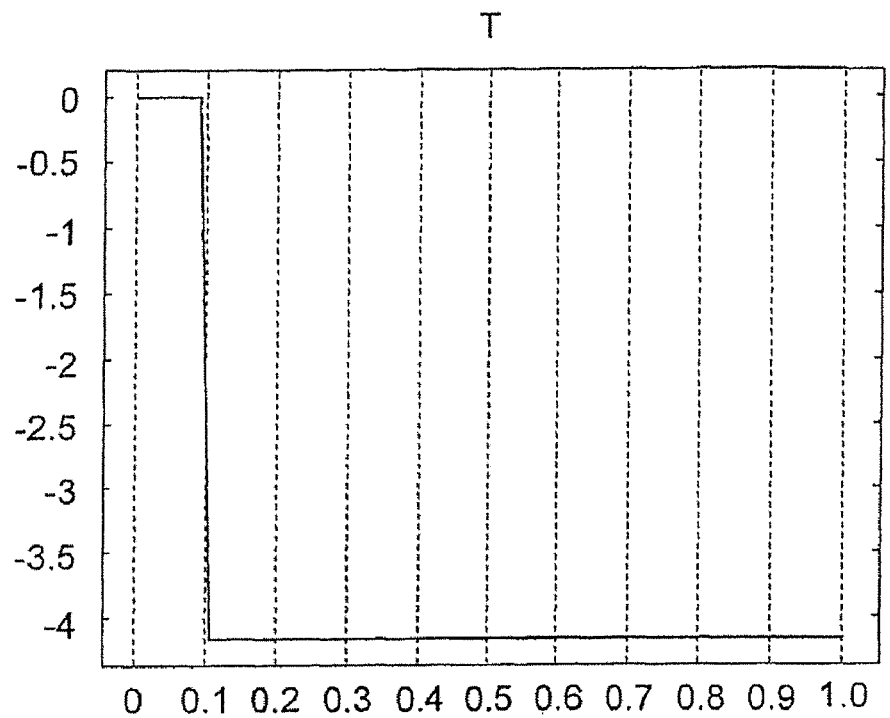
FIG. 12 shows a graph of the temperature interference due to an introduced pressure transient.

In this model example the density ρ is approximated to a constant value since comparatively small pressure and temperature variations are studied. Now solving the equation Eq. 2 for a case without any heat transmission term and an introduced pressure transient Δp=5000 [Pa]=50 cmH2O results in the values plotted in the graph of FIG. 12. This corresponds to an infinite size of the measurement chamber or to a heat conductivity λ=0. In FIG. 12 the interference in terms of temperature variation is plotted as a function of time where values for time is on the horizontal axis and values for temperature interference in degrees Celsius is on the vertical axis. As shown in the graph the input pressure transient of Δp=5000 [Pa]=50 cmH2O entails a very fast decrease in temperature of about 4 degrees Celsius.

Thus in this example, a pressure decrease of 50 cmH2O would cause a temperature variation in the form of a decrease in the range of 4 degrees Celsius (° C.). Then it is calculated a maximum allowable time lag for thermal exchange between the gas mixture and the measurement apparatus dependent on the maximum allowable error in the determined proportion of a gas in the gas mixture and the magnitude of occurring temperature variations in the gas mixture. In the current example, a maximum allowable time lag, expressed as the time constant, for thermal exchange between the gas mixture and the measurement apparatus would be about 0.050 seconds. With these requirements the measurement apparatus is adapted such that the time lag for thermal exchange between the gas mixture and the measurement apparatus is less than or equal to ($\leqq$) the calculated maximum allowable time lag for thermal exchange.

Applying the basic result of the dimensioning method, the method further comprises the step of selecting a combination of shape, size and material of a measurement chamber in the measurement apparatus in relation to properties of the gas mixture such that the time lag for thermal exchange between the gas mixture and the measurement apparatus is less than or equal to ($\leqq$) the calculated maximum allowable time lag for thermal exchange.

In embodiments of the invention it is often advantageous to apply a signal filter on signals from the ultrasound detectors, and to also take account of the time lag, preferably the time constant, of the filter in dimensioning the measurement apparatus. An embodiment of the method therefore further comprises the step of selecting a time lag of a signal filter for application on a signal from an ultrasound detector in the measurement apparatus dependent on predetermined requirements on the response time of the measurement apparatus. Consequently this embodiment comprises the maximum allowable time lag for thermal exchange between the gas mixture and the measurement apparatus to be calculated also dependent on the time lag of a signal filter for application on a signal from an ultrasound detector in the measurement apparatus.

In an embodiment in which account is taken of also the time lag of the signal filter, calculating a maximum allowable time lag for thermal exchange between the gas mixture and the measurement apparatus would comprise the following steps of:

calculating the magnitude of occurring error in the determined proportion of a gas in the gas mixture dependent on the magnitude of occurring temperature variation in the gas mixture;

calculating a maximum allowable detected temperature variation due to pressure variation;

determining a relation between the maximum allowable detected temperature variation and the maximum occurring temperature variation in the gas mixture due to pressure variations;

determining a relation between the time lag for thermal exchange between the gas mixture and the measurement apparatus and the time lag of a signal filter for application on a signal from an ultrasound detector in the measurement apparatus;

determining a relation between said temperature relation and said time lag relation; and calculating a maximum allowable time lag for thermal exchange between the gas mixture and the measurement apparatus dependent on said relation between said temperature relation and said time lag relation.

As mentioned above, a preferred measure on the time lag is the time constant, i.e. according to the definition the time required to reach 63.2 percent of the total thermal exchange.

Having determined the requirements on the thermal exchange properties of the measurement apparatus, the inventive concept comprises different approaches for achieving the sufficient thermal exchange efficiency.

In one embodiment the required thermal exchange speed is achieved by decreasing or minimizing, in relation to other design parameters, the distance between gas molecules and surfaces of the matter that defines the cavity. More specifically, that is the matter that surrounds or is surrounded by the gas in the chamber cavity. In one variety of this embodiment, the surface area of the thermal buffering material is enlarged in the sound propagation region of the chamber cavity.

Figure 2:
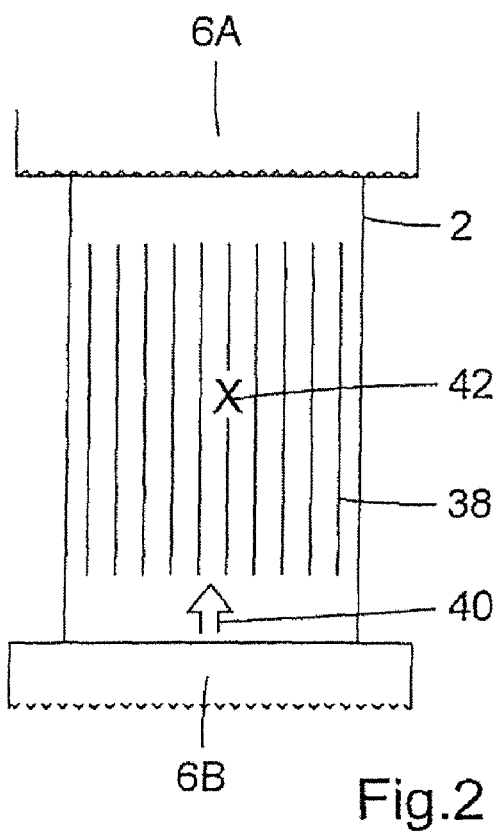
FIG. 2 shows an embodiment of the invention with solid structure flanges in the sound propagation region of the measurement chamber.

For example, as illustrated in the embodiment of FIG. 2, the measurement chamber 2 can be provided with flanges 38 of thermal buffering material positioned in the sound propagation region. Preferably the flanges 38 are mounted in parallel with the direction of sound propagation 40 between transducers 6A, 6B in order not to decrease the sound pressure. Similarly, the main gas flow direction 42 through the measurement chamber should be in parallel with the flanges in order not to disturb the flow rate through the chamber. In FIG. 2 the gas flow direction 42 is into the paper, and thus orthogonal to the sound propagation direction 40. Experimental tests with a measurement chamber provided with steel flanges having a thickness of about 1 millimeter (mm) and an intermittent internal distance of about 2 millimeters (mm) have shown that temperature variations in ventilator operation were evened out to such an extent that temperature related effects were negligible. No measurement and compensation of the temperature variations were required and only a relatively slow measurement of the basic gas temperature was needed in order to achieve accurate results in the calculation of gas concentration.

Figure 3:
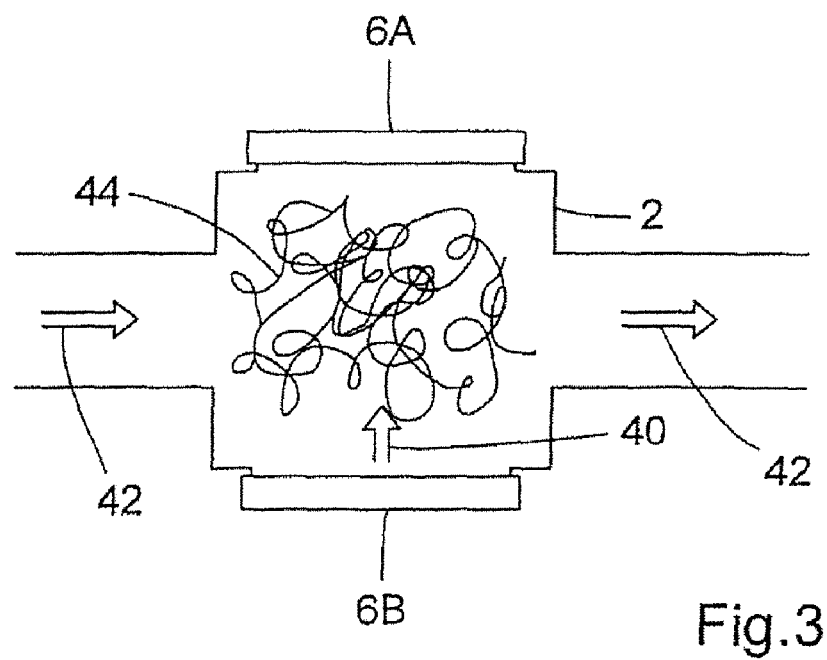
FIG. 3 shows an embodiment of the invention with a porous structure in the sound propagation region of the measurement chamber.

In another exemplifying embodiment shown in FIG. 3, the chamber 2 is in its sound propagation region provided with a porous structure 44 of solid material such as wire wool or a sponge structure, for example made of steel or some other metal or similarly heat conductive material. The gas flows through and surrounds the porous structure 44 and thus a small distance from gas molecules to structure surfaces is achieved. The porous structure should be provided such that ultrasound travels through the porous structure without any significant disturbance and with a small flow resistance.

In a third exemplifying embodiment the chamber cavity is shaped as a pipe with a small diameter, which renders a small distance from gas molecules in the cavity to the inner walls of the pipe. Preferably, the inner pipe shape is cylindrical but other cross sections are also conceivable. In a practical implementation of this embodiment a partial gas flow is diverted from the main gas flow to the measurement chamber in order to thermally buffering and measuring an appropriate gas volume. This concept is applied in a presently preferred embodiment of the invention shown in FIGS. 4 to 7. A model has been determined in order to find a suitable diameter of the pipe shaped chamber cavity. This model is based on studying a relative level of interference on the measurement accuracy due to temperature variations caused by pressure transients. It is assumed that the relative temperature interference level T(r,t) decreases exponentially according to the equation:

$$T(r, t) = \Delta T_0 \exp\left(-\frac{t}{\tau}\right) g\left(\frac{r}{r_0}\right) \quad \text{Eq. 3}$$

where r0 is the inner radius of a cylinder, r is a radius in the space in the cylinder, i.e. in the pipe shaped chamber, $g(r/r_0)$ is a temperature distribution in the space in the cylinder and $\tau$ is a time constant.
The time constant $\tau$ is $$\tau = 0.1729 \frac{\rho C_p}{\lambda} r_0^2 \qquad \text{Eq. 4}$$

where $\rho$ is density, Cp is specific heat at constant pressure and $\lambda$ is heat conductivity with values as described in Table 1 above.

Figure 13:
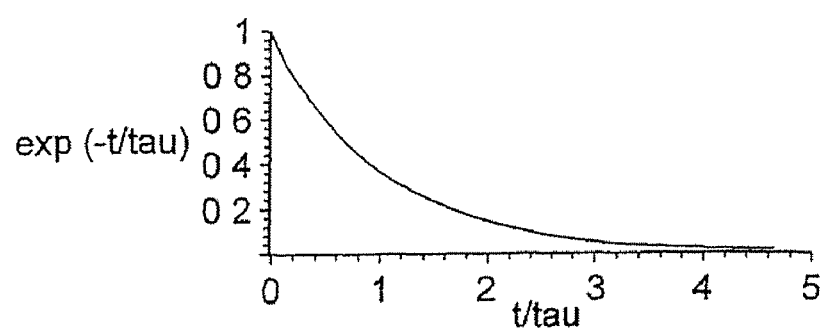
FIG. 13 shows a graph of the decrease of relative temperature interference that is plotted over time normalized with the time constant.

The graph in FIG. 13 shows an example of a relation in the shape of the curve for the decrease of relative temperature interference that is plotted over time normalized with the time constant. After 1 time constant the interference level has decreased to about 36 percent of the initial level.

Using these equations in modelling calculations show relations between different pipe radius r0 [millimeters] and the relative temperature interference level after a time constant of $\tau$ (tau) [s] due to pressure variations compared with a nominal level without any temperature equilibrating according to the invention. In the below table, these parameters are listed at two points in time t=0.01 [s] and t=0.1 [s], respectively, after an introduced pressure transient. For example, it is shown in the table that a pipe with a radius of 3.0 mm has a time constant tau=0.0765 and a relative temperature interference level of 0.877 after 0.01 seconds and 0.271 after 0.1 seconds.

TABLE 2

| $r_0$ [mm] | tau [s] | exp(−0.01/tau) | exp(−0.1/tau) |
|---|---|---|---|
| 1.0 | 0.0085 | 0.308 | 0.0000078 |
| 1.5 | 0.0191 | 0.593 | 0.00536 |
| 2.0 | 0.0340 | 0.745 | 0.0528 |
| 2.5 | 0.0531 | 0.828 | 0.152 |
| 3.0 | 0.0765 | 0.877 | 0.271 |
| 4.0 | 0.136 | 0.929 | 0.479 |
| 5.0 | 0.213 | 0.954 | 0.625 |
| 6.0 | 0.306 | 0.968 | 0.721 |
| 7.0 | 0.417 | 0.976 | 0.787 |
| 8.0 | 0.544 | 0.982 | 0.832 |

It can be shown that for a gas mixture of 50 percent O2 and 50 percent N2 the error in determined O2 concentration is about 2.5 percentage units per degree Celsius of temperature variation. So, in the previous example with a radius of 3.0 mm and a relative interference level of 0.877 after 0.01 seconds, the error in the determined O2 concentration would be $\Delta XO2 = 2.5 \times 0.877 \approx 2.2$ percent.

In an application of the invention in an O2-sensor for a breathing apparatus, pressure variations with extreme values of up to about 100 cmH2O have to be accounted for in the dimensioning process. This would, in the same manner as in the calculations above result in temperature variations of up to about 8 degrees Celsius, which in its turn by calculating 2,5 [percentage units error in O2 concentration/degree Celcius temperature variation]×8 [degrees Celsius] results in an error interference of up to about 20 percentage units of O2 due to pressure induced temperature variation. By means of signal filtering this interference can be reduced to a more tolerable level of about 3 percents. That is the filter shall reduce the error to a fraction with a reduction factor of 3 percent/20 percent=0.15. A signal filter is thus applied on the signal from the ultrasound sensor. The signal filter limits the speed of the ultrasound sensor with regard to signals that originate from real variations in O2 concentration. With a large filter time constant $\tau f$ the smaller is the influence on the O2 concentration from pressure induced temperature variation. With this configuration, the error in the measured O2 concentration is thus affected on one hand by the thermal time constant $\tau$ of the measurement chamber and on the other hand by the signal filter time constant $\tau f$. Using a more detailed version of the dimensioning method with the signal filter briefly described above and applied for determining required dimensions of a measurement chamber, it is determined a relation between the time constant $\tau f$ of the signal filter, the time constant $\tau$ of the measurement chamber and a reduction factor $\eta$ that corresponds to a reduction factor of how much the filter reduces the maximum interference. From this relation (not shown in detail) it is in this example determined that for a reduction factor 0.15 the time constant $\tau$ of measurement chamber$\leqq 0.235 \times$time constant of the signal filter $\tau f$. In practice, the connection $\tau \leqq 0.235 \times \tau f$ is for example found as a point on the graph that describes the relation of the interference reduction factor as a function of the time constant ratio, i.e. $\eta(\tau f/\tau)$. With a slow filter having a time constant of 20 seconds, the maximum time constant of the measurement chamber would thus be 0.235×20=4.7 seconds. Calculating the inner diameter of a metal pipe as a decisive dimensioning parameter and assuming the gas mixture to be air, the resulting requirement is that the maximum inner diameter is 47 millimeters.

When carrying out the invention there are different design factors and parameters to consider in order to provide a thermal exchange effect with a sufficient efficiency in accordance with the invention. In one embodiment of the inventive concept a selected structural design is dimensioned with regard to for example diameter, wall thickness, weight or heat conductivity by means of the following method. The variation of pressure that can occur in a specific application of the invention is measured, with particular attention given to unfavourable pressure cases. A simulation of consequences of one or more selected design parameters on for example time constant and temperature interference level is carried out and a maximum temperature interference level is determined. The temperature deviation or temperature interference level is translated into an error in a resulting calculated gas concentration or gas flow. A maximum allowable error, thus alternatively expressed as deviation or interference level, for a resulting measured gas concentration level is predetermined, for example maximum 3% error in O2-rate. Thereafter, the selected design parameter, for example diameter of a pipe, is calculated dependent on the predetermined maximum gas concentration error. If for example the required heat conductivity is the selected design parameter to be dimensioned, the corresponding calculation is made also dependent on a for example a predetermined pipe diameter. This concept is similar to the modelling example given above.

Figure 4:
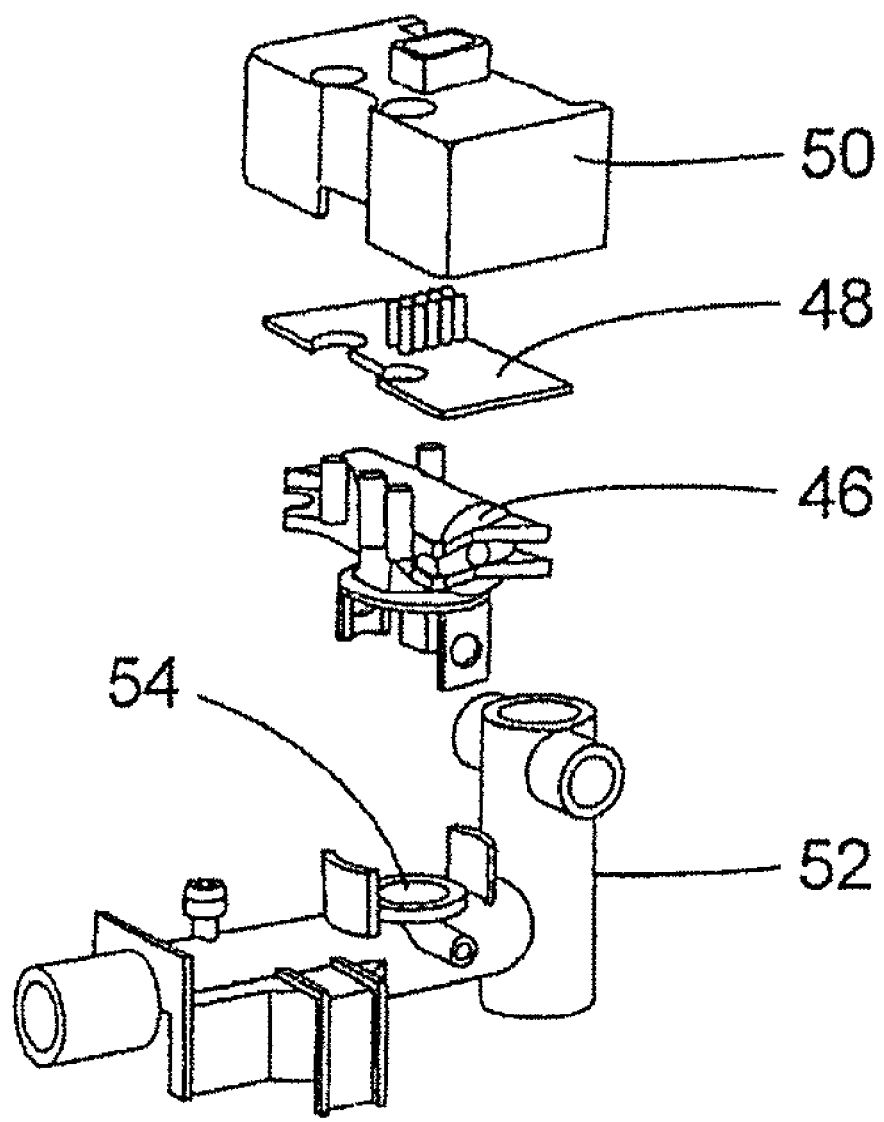
FIG. 4 shows an exploded view of a measurement device assembly according to an embodiment of the invention.

FIG. 4 shows an exploded view of main parts of an embodiment of the invention realised as a measurement device assembly comprising a sensor housing 46 with a measurement chamber that is not visible in FIG. 4, a circuit board 48 with connectors to external wiring and a protective cover 50 devised to cover the sensor housing 46 and the circuit board 48. The sensor housing 46 is devised to be mounted on a main gas flow pipe 52 covering and partly intruding into the main gas flow via an opening 54 in the gas flow pipe 52. A part of the gas flow is thereby conducted into the measurement chamber of sensor housing 46.

Figure 5:
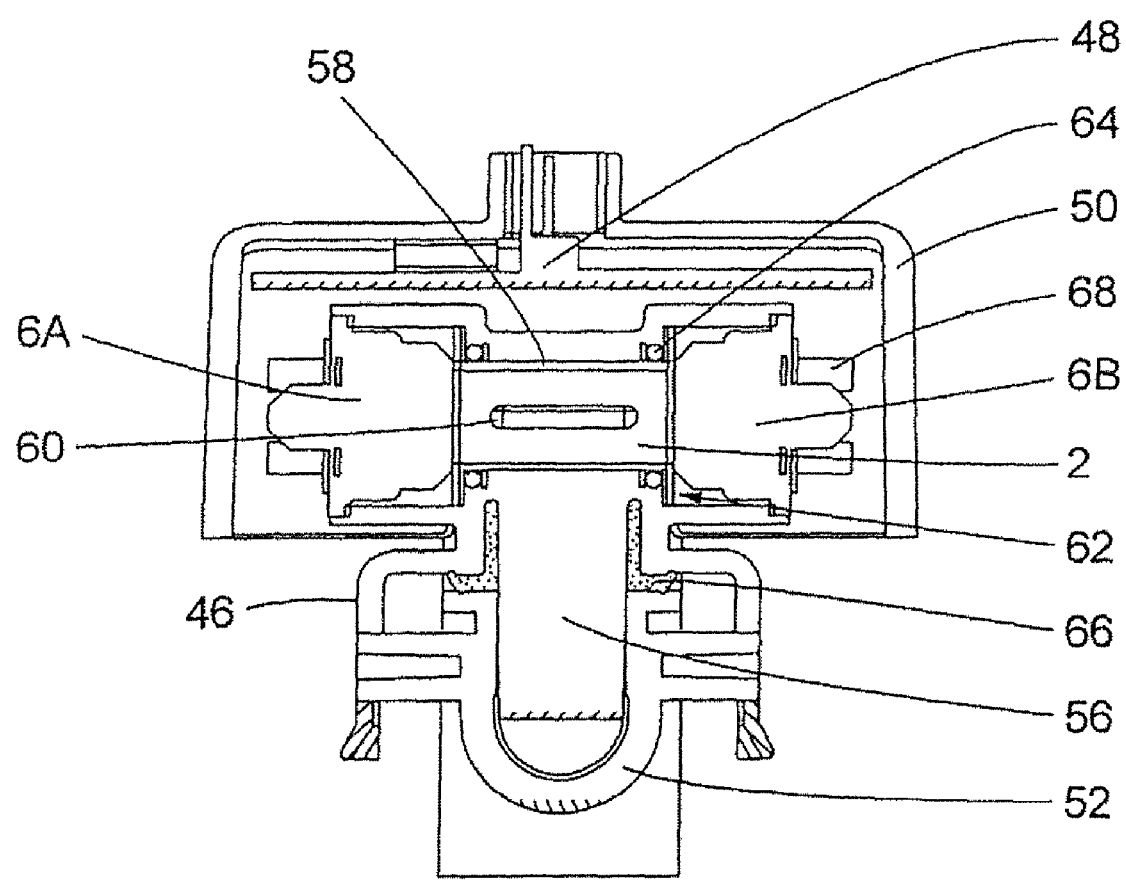
FIG. 5 shows a cross section of the measurement device assembly in the embodiment of FIG. 4.

FIG. 5 shows a cross section of the measurement device assembly mounted on a main gas flow pipe 52 according to FIG. 4. A sensor housing 46 is provided with a lip member 56 projecting into the main gas flow pipe 52 and conducting gas to a measurement chamber 2. The measurement chamber 2 is spatially defined by a cylindrical pipe 58 comprising mutually opposing elongate inlet and outlet openings 60 for the gas positioned along the mantle of the cylinder. The elongate form of the inlet and outlet opening are devised to minimize affecting the ultrasound propagation pattern that may occur in connection with sudden area changes in a gas flow. More specifically, sound pulse bounces at the area changes are decreased or even avoided, and thereby destructive interference with the sound propagation patter due to such sound pulse bounces is avoided. In operation, the gas flows along the lip member and to and from the pipe cavity via the inlet and outlet openings 60. In FIG. 5 only one of the inlet and outlet openings is visible. Ultrasound transducers 6A, 6B are positioned at each end opening of the pipe such that the active surface of the transducer covers the end opening of the pipe at each respective end. A washer 62, having the function of a dampening seal, seals to prevent leakage between the active surface of the transducer and the chamber pipe 58. O-rings 64 seal between the chamber pipe 58 and the sensor housing 46 and a collar shaped sealing 66 seals between sensor housing 46 and main gas flow pipe 52. A springy shackle piece 68 at each side straps the transducers 6A, 6B against the chamber pipe 58. It is clear from FIG. 5 that most of the components in the sensor housing appear in pairs that are mounted in a symmetrical fashion around the chamber pipe 58. A circuit board 48 is placed on top of the sensor housing 46 and finally the assembly is covered by a protective cover 50.

Figure 6:
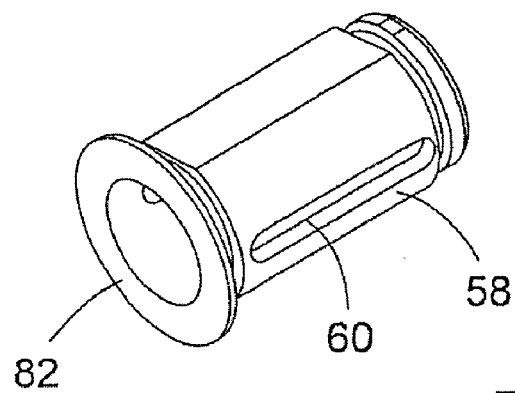
FIG. 6 shows a perspective view of a measurement chamber pipe.
Figure 7:
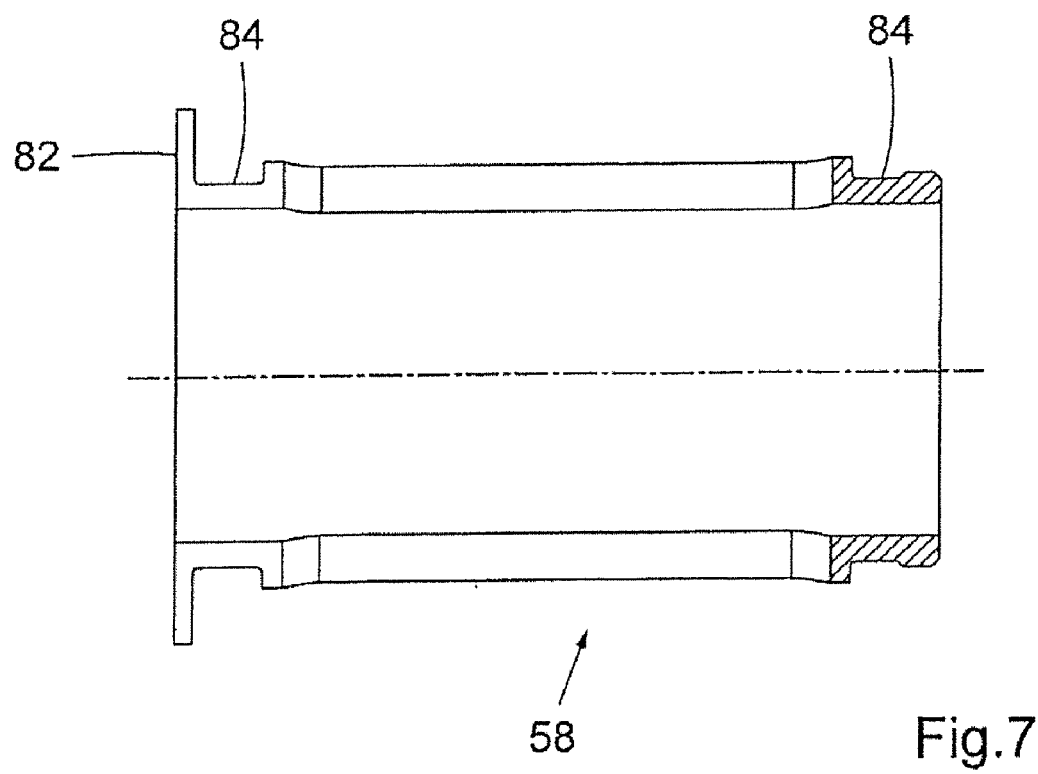
FIG. 7 shows a cross section side view according to the embodiment of FIG. 5.
Figure 8:
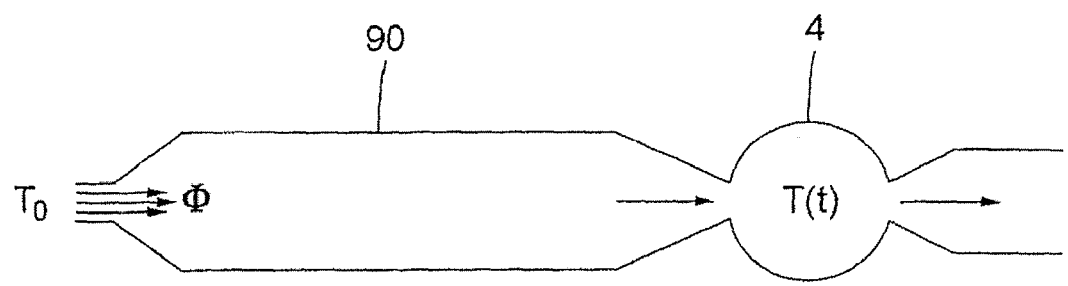
FIG. 8 shows an outline of an embodiment with an equilibrating upstream gas channel portion.

FIGS. 6 and 7 show the chamber pipe 58 in more detail. The chamber pipe is at one of the ends provided with a flange 82 having the function of a position stop when the pipe 58 is mounted in the sensor housing. At each end of the pipe 58 there is a recess 84 for receiving the O-ring seal 64 (Cf. FIG. 5). Elongate inlet and outlet openings 60 are as mentioned above provided along the mantle of the pipe 58. The dimensions of the chamber pipe are preferably optimized with regard to temperature variations as well as to signal/noise level. This exemplifying embodiment is designed for an inspiration channel of a breathing apparatus with a typical gas flow rate in the range of 0-200 l/min in the main flow through the inspiration channel, a typical operating gas temperature in the range of 15-50° C. and typical pressure variations in the range of 0-140 cmH2O. This embodiment of the chamber pipe preferably has an inner diameter in the range of 9 mm and an outer diameter in the range of 12 mm, rendering a material thickness of about 3 mm in the major part of the chamber wall and a maximum distance from a gas molecule to an inner surface of about 4.5 mm. The material is stainless steel having heat conductivity in the range of 50 W m$^{-1}$ K$^{-1}$ In an embodiment of the invention applied in an environment where the gas flow is large in relation to the volume of the measurement chamber cavity, there is preferably provided an upstream gas channel portion devised for equilibrating temperature gradients in accordance with the inventive concept. Thereby the risk that the gas portion in the chamber is exchanged with a speed that exceeds the speed of the temperature equilibration in the chamber is eliminated. Such an upstream gas channel portion is thus preferably devised with a heat conductive material in a cross section dimension that is small compared with the main flow dimensions. FIG. 8 shows an outline drawing of this embodiment, with a temperature equilibrating channel portion 90 positioned upstream the measurement chamber cavity 4 and devised to level out the temperature T0 of inflowing gas before it enters the measurement chamber. In the embodiment of previously explained FIG. 5, the lip member 56 together with the surrounding structure forms such a temperature equilibrating channel portion.

Another aspect in acoustic sensors in accordance with the invention deals with the problem of expansion in the measurement chamber. Measuring the speed of sound c by means of an acoustic sensor is based on measurement of the time t it takes for a sound pulse to travel a known distance s, and calculating $c=s/t$. It is therefore required to have an accurate and stable measure of the measurement distance. For example, in measuring gas concentration via sound speed detection in a gas mixture of air and oxygen on a measurement distance of 18 mm a change of 10 micrometers in the measurement distance renders an error of about 1% in the oxygen concentration unit. Expansion of the measurement distance can occur due to thermal expansion in the chamber or in the transducer and due to pressure changes in the measurement chamber.

The thermal expansion occurs in the chamber enclosing structure and in the ultrasound transducer itself. The material for the chamber enclosing structure is in accordance with the invention dealt with by selecting a material with as low linear temperature expansion coefficient as possible in relation to other design parameters. For example, aluminium with the linear thermal expansion coefficient of 22.2 (m/m·K×10$^{-6}$) or steel with 13.0 (m/m·K×10$^{-6}$) can be used for the chamber.

The ultrasound transducer is composed of layers of different materials with an active ultrasound emitting surface on an adaptation material, a layer of dampening material and a layer of silicone rubber all mounted on a flange that is normally used for mounting the transducer against the rim of a recess. All these layers expand or shrink dependent on temperature changes in the environment or in the gas, or due to ultrasound generation and thereby incur errors in measurements. In accordance with the invention, and as shown in the schematic drawing of FIG. 9, this effect is eliminated by mounting the transducers such that the active surfaces 94 of the respective transducer 6A/6B cover the end openings of the pipe shaped chamber cavity 4. Dimension changes in the material making up the transducer are thereby negligible since the position of the active surface is kept constant. The active surface 94 rests against a thin acoustically dampening seal in the shape of a washer 62 positioned between the end cross section of the chamber wall 97. The dampening seal washer 62 is preferably made of silicone rubber, for example with a thickness of about 0.7 millimeters. The dampening seal washer 62 addresses a fourth aspect of the invention, namely to eliminate structure borne sound. Due to its small thickness the silicone seal has a negligible length expansion due to pressure as well as temperature.

Figure 9:
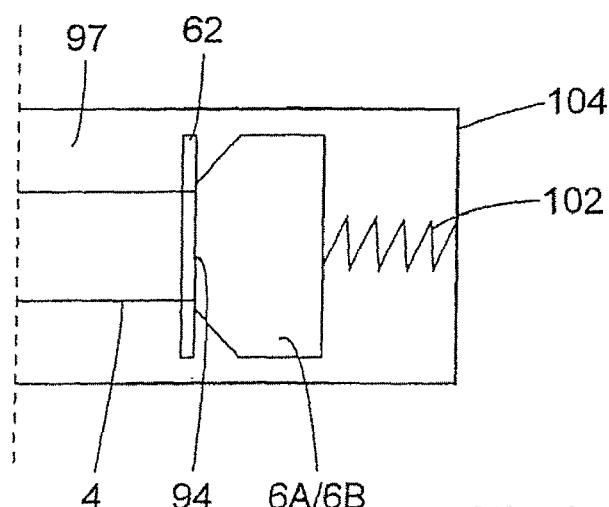
FIG. 9 shows schematically how the transducer is mounted to the measurement chamber in accordance with an aspect of the invention.

Further, the transducer is mounted with a spring device 102 pressing the transducer against the dampening seal washer 62. In FIG. 9, the spring is illustratively seated against a shackle or strap 104 that is rigidly fastened in relation to the chamber structure. In the embodiment shown in FIG. 6, the shackle piece 68 is itself embodying a spring. The spring device should be devised with a spring force that exceeds the largest pressure pulses that occur in the measurement chamber and thereby eliminates displacement of the transducer and pressure dependent expansion of the measurement distance.

An advantage with this embodiment is that it enables a small size measurement chamber. The small size simplifies the temperature measurement in connection with gas concentration measurement, since a small sound propagation region renders a more homogenous gas temperature. This in its turn enables that the gas temperature can be measured in a point instead of over the whole region. This concept can be used as illustrated in an embodiment of the present invention or independently in conjunction with other configurations of ultrasound transducers.

Another approach of dealing with expansion in the chamber material is to design the measurement chamber with a spherical shape, entailing that the thermal expansion of the chamber enclosure will be equal in all directions. A drawback with this embodiment is that a sphere is the geometrical shape that renders the smallest possible surface area in relation to the volume. This embodiment is therefore preferably provided with extra thermally buffering material in order to achieve a sufficiently efficient thermal exchange with the gas content of the chamber. This may for example be realised by means of thicker chamber walls, flanges or a porous structure inside the chamber cavity.

Figure 10A:
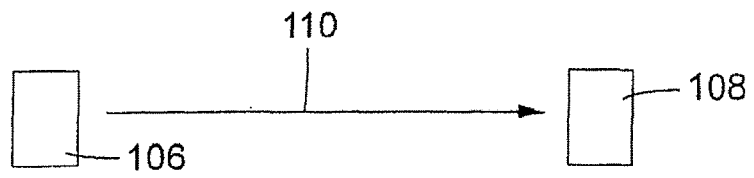
FIG. 10A-D illustrate how an nth echo of an ultrasound pulse is detected.
Figure 10B:
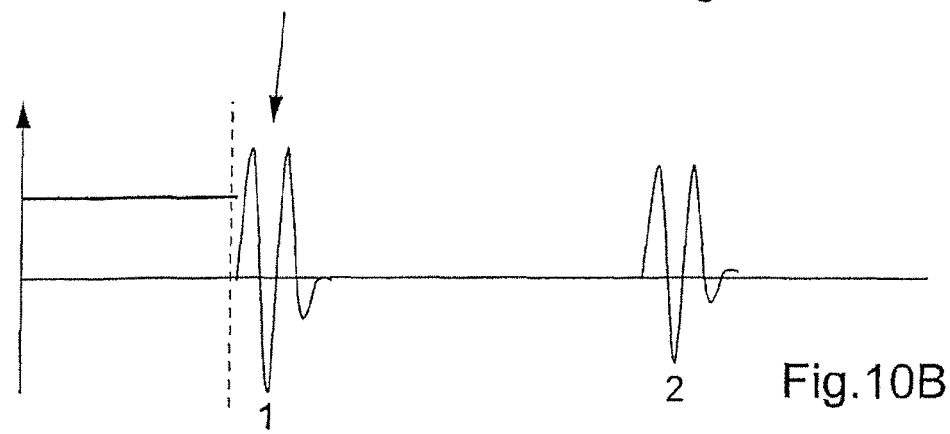
Figure 10C:
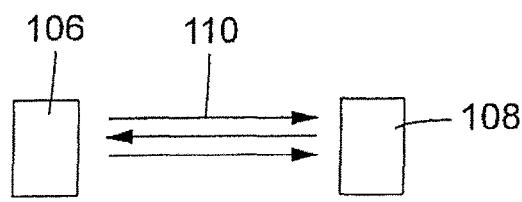
Figure 10D:
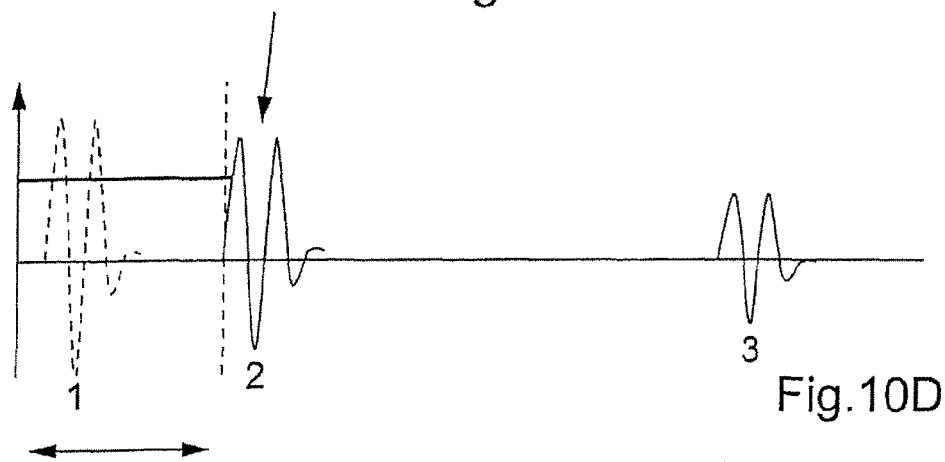

A further aspect of the invention is concerned with the problem of achieving a satisfying resolution in the ultrasound measuring in spite of a short measurement distance. This is solved in accordance with the invention by allowing a sound pulse to bounce between the pair of transducers before a read out of the travel time is made. In effect, thus a reflected signal that has traveled a longer distance is detected and timed. FIGS. 10A-10D illustrate the invention. FIG. 10A illustrates for the sake of the example an emitting ultrasound transducer 106 that sends an ultrasound pulse over a measurement distance 110 of for example 6 centimeters to a receiving transducer 108. FIG. 10B illustrates the sound pulse emitted at 1 with a first emitted amplitude and received at 2 with a second lower amplitude due to energy loss during the travel through the gas. In FIG. 10C the emitting and the receiving transducers are positioned with a shorter intermediate distance of for example 2 centimeters. The sound pulse is as illustrated by the arrows allowed to bounce or echo twice between the transducers and is detected by the receiving transducer after having traveled three times the distance between the transducers. As illustrated in FIG. 10D, the receiver is preferably dampened during emission of the sound pulse in time period 1 in order to counteract interfering oscillations. The pulse bounces first time in period 2 and second time in period 3 whereupon it is detected by the receiving transducer. In general, the nth echo is detected and appropriate consideration is taken to signal dampening. In a preferred embodiment, however, dependent on the design of the measurement chamber, the second echo is detected. Detection of an nth echo, e.g. the second, of the ultrasound pulse entails that the ultrasound travels a longer distance and thus improves the resolution of measurements in a small size measurement chamber.

Figure 11A:
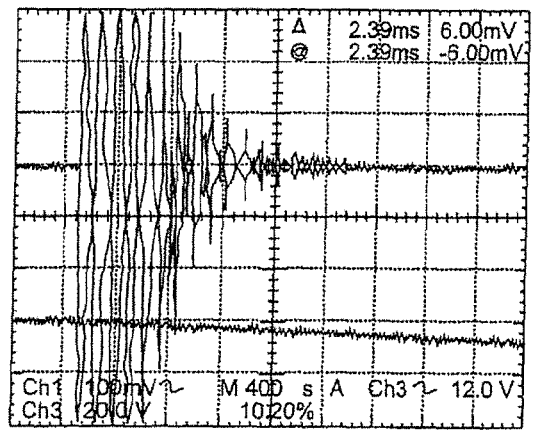
FIG. 11A-D illustrate how the emitting transducer is excited in accordance with an aspect of the invention.
Figure 11B:
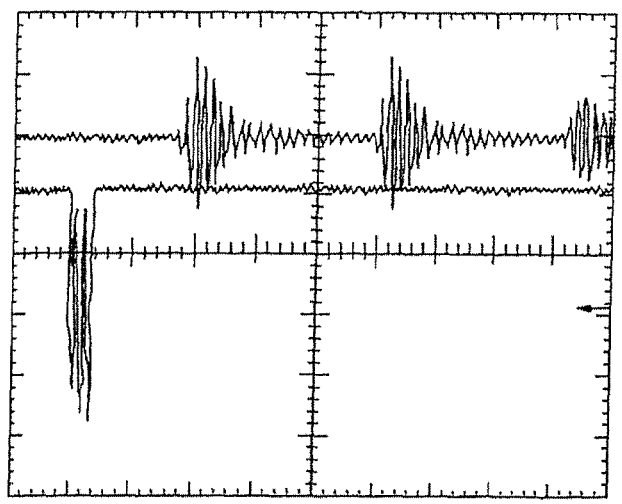
Figure 11C:
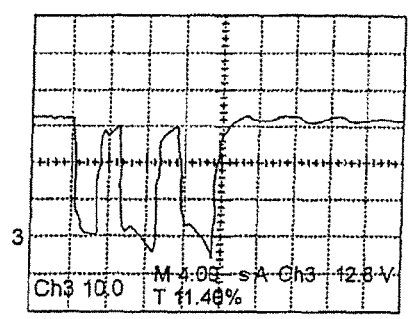
Figure 11D:
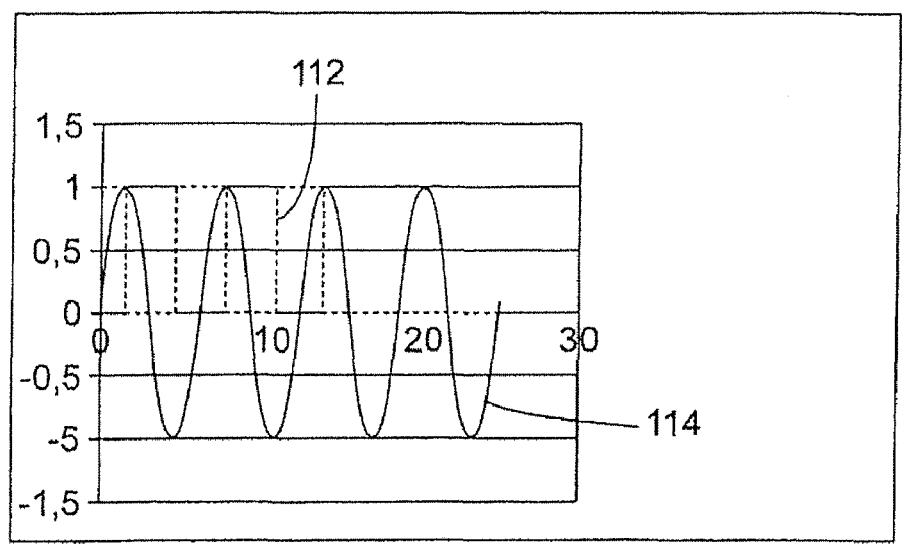

Yet another aspect of the invention deals with the problem of achieving appropriate signal patterns from the sensor arrangement. In accordance with an embodiment of the invention, the emitting transducer is operated to emit an ultrasound pulse with a repetition frequency of 200 Hz. The transducer is in this connection excited to oscillate and emit pulses that in fact are bursts of pulse trains for example comprising 3 pulses each having the duration of 2.25 periods thus corresponding to 0.0050 seconds. In order to decrease transients and render a harmonious transient steady-state process, the transducer exciting voltage is controlled to oscillate and have a high voltage only during the elevation period of the oscillations of the transducer. That is when the transducer output has a positive derivative and thus the first oscillation of the exciting voltage has a length of only ¼ pulse period. This is illustrated in FIGS. 11A-11D. FIG. 11A is a screen dump from an exemplifying oscilloscope measurement illustrating how a sound pulse bounces between the transducer surfaces in the measurement chamber as detected by the receiving transducer. The sound has been dampened out after about 2.4 milliseconds and a new pulse emission can start. In FIG. 11B the upper plot shows detected ultrasound pulses and lower plot shows the excitation voltage input to the emitting transducer. The time from the start of the emission until for example the second echo is received by the receiver is measured by means of a timer in the microprocessor as explained above. FIG. 11C shows a partial enlargement of the excitation oscillation in FIG. 11B. The first oscillation is only a ¼ pulse period long whereas the subsequent oscillations have a length of a ½ pulse period, thus the applied signal deviates from the resonance frequency of the transducer in a mathematical sense. This is also shown in the schematic illustration of the excitation oscillation in relation to the output of the emitting transducer. The exciting voltage is in accordance with FIG. 11D input to the transducer in the shape of a burst of square wave oscillations 112 starting with a ¼ pulse period thus having a high voltage during positive derivative portions of the transducer output signal 114. This concept can be used as illustrated in an embodiment of the present invention or independently in conjunction with other configurations of ultrasound transducers.

The inventive concept can also be applied in measurement of gas flow by means of ultrasound. An ultrasound based flow meter makes use of the difference between the speed of sound upstream and downstream in a measurement region. The average of an upstream measurement value and a downstream measurement value gives an indirect measure on the gas composition and the gas temperature. With a temperature buffer according to the invention applied in the measurement region of a flow meter, the measurement values will be a measure only on flow and gas composition. This can for example be used in determining functional residual capacity (FRC) of the lungs of a patient. The time of specific measurement samples does not have to be synchronised with temperature measurements.

Although modifications and changes may be suggested by those skilled in the art, it is the intention of the inventor to embody within the patent warranted heron all changes and modifications as reasonably and properly come within the scope of his contribution to the art.

I claim as my invention:

1. An apparatus for determining a proportion of gases in a mixture, comprising:
   a measurement chamber having a chamber defining structure, a gas inlet, and a gas outlet;
   an ultrasound source and an ultrasound detector mounted such that the ultrasound source is capable of transmitting ultrasound through the chamber to the ultrasound detector;
   a temperature sensor mounted such that the sensor is capable of sensing the temperature in the chamber; and
   said chamber defining structure being configured to minimize a distance between gas molecules in the chamber and surfaces of the chamber defining structure, forming a thermal buffer having an efficient thermal exchange with the gas molecules.

2. An apparatus as claimed in claim 1, wherein said chamber defining structure is configured such that a maximum distance from any gas molecule within the chamber, and a surface of the chamber defining structure, is approximately 4.5 mm.

3. An apparatus as claimed in claim 1, wherein said chamber is shaped as a pipe having an inner diameter of approximately 9 mm.

4. An apparatus as claimed in claim 3, wherein said pipe is cylindrical.

5. An apparatus as claimed in claim 1, wherein said chamber comprises chamber walls having a material thickness of approximately 3 mm.

6. An apparatus as claimed in claim 1, wherein said chamber defining structure is comprised of metal.

7. An apparatus as claimed in claim 1, wherein said chamber defining structure is comprised of steel.

8. An apparatus as claimed in claim 1, wherein said gas inlet and said gas outlet are elongated.

9. An apparatus as claimed in claim 1, wherein said measurement chamber is shapes as a cylindrical pipe having opposing elongate inlet and outlet openings respectively located along a mantel of said cylinder.

10. An apparatus as claimed in claim 1, wherein said measurement chamber comprises thermal buffering material located in a propagation path of said ultrasound.

11. An apparatus as claimed in claim 10, wherein said thermal buffering material are formed as flanges in said propagation path.

12. An apparatus as claimed in claim 11, wherein said flanges are located in parallel with a primary gas flow direction through said measurement chamber and a direction of propagation of said ultrasound in said propagation path, said primary gas flow direction being orthogonal to said propagation direction.

13. An apparatus as claimed in claim 10, wherein said measurement chamber comprises a porous structure of thermal buffering material in a propagation path of said ultrasound.

14. An apparatus as claimed in claim 1, comprising an upstream gas channel portion comprised of heat conductive material.

15. An apparatus as claimed in claim 1, comprising an upstream gas channel portion comprised of heat conductive material, and having a cross-section dimension that is small compared to dimensions of a primary gas flow channel.

* * * * *